(12) United States Patent
Glaug et al.

(10) Patent No.: US 7,166,094 B2
(45) Date of Patent: Jan. 23, 2007

(54) MULTIPLE LAYER ABSORBENT ARTICLE

(75) Inventors: Frank S. Glaug, Chester Springs, PA (US); Robert Theodore Cole, Jackson, NJ (US); Ryan K. Hood, Drexel Hill, PA (US)

(73) Assignee: Tyco Healthcare Retail Services AG, Schaffhausen (CH)

( * ) Notice: Subject to any disclaimer, the term of this patent is extended or adjusted under 35 U.S.C. 154(b) by 567 days.

(21) Appl. No.: 10/156,598

(22) Filed: May 28, 2002

(65) Prior Publication Data

US 2003/0225383 A1 Dec. 4, 2003

(51) Int. Cl.
*A61F 13/15* (2006.01)

(52) U.S. Cl. .................. 604/385.17; 604/385.101; 604/380; 604/385.21; 604/378

(58) Field of Classification Search ......... 604/385.101, 604/385.17, 371, 378, 385.21, 380, 385.01
See application file for complete search history.

(56) References Cited

U.S. PATENT DOCUMENTS

| | | | | |
|---|---|---|---|---|
| 2,043,325 A * | 6/1936 | Jackson, Jr. ............... | 604/375 |
| 2,331,271 A | 10/1943 | Gilchrist ................. | 128/284 |
| 2,787,271 A | 4/1957 | Clark .................... | 128/290 |
| 3,071,138 A | 1/1963 | Garcia ................... | 128/290 |
| 3,670,731 A | 6/1972 | Harmon .................. | 128/284 |
| 3,744,494 A | 7/1973 | Marsan .................. | 128/287 |
| 3,800,797 A | 4/1974 | Tunc .................... | 128/290 R |
| 3,805,790 A | 4/1974 | Kaczmarzyk et al. ... | 128/290 R |
| 3,848,595 A | 11/1974 | Endres .................. | 128/284 |
| 3,881,490 A | 5/1975 | Whitehead et al. ...... | 128/287 |
| 4,029,100 A | 6/1977 | Karami .................. | 128/284 |
| 4,059,114 A | 11/1977 | Richards ................ | 128/287 |
| 4,282,874 A | 8/1981 | Mesek ................... | 128/287 |
| 4,285,343 A | 8/1981 | McNair .................. | 128/287 |
| 4,321,924 A | 3/1982 | Ahr ...................... | 128/287 |
| 4,323,069 A | 4/1982 | Ahr et al. ............... | 128/287 |
| 4,463,045 A | 7/1984 | Ahr et al. ............... | 428/131 |
| 4,556,146 A | 12/1985 | Swanson et al. ......... | 206/440 |
| 4,573,986 A | 3/1986 | Minetola et al. ......... | 604/366 |
| 4,589,876 A | 5/1986 | Van Tilburg ............ | 604/385 R |
| 4,601,868 A | 7/1986 | Radel et al. ............. | 264/504 |
| D287,637 S | 1/1987 | Grasso .................. | D24/51 |
| 4,639,254 A | 1/1987 | LeGault et al. ......... | 604/385 R |

(Continued)

FOREIGN PATENT DOCUMENTS

EP 0 998 893 A2 5/2000

(Continued)

*Primary Examiner*—Jacqueline F. Stephens

(57) ABSTRACT

An absorbent article is provided having an absorbent core with an absorbent pledget adhered to the body-facing side of the core between the core and the body-facing surface of the article. The pledget has a greater structural stiffness and a reduced surface area relative to the core. The absorbent article has a fluid permeable coverstock including a bicomponent fiber. An hourglass-shaped absorbent pledget is disposed between the core and the coverstock. The pledget includes airlaid material adhered to the body-facing side of the absorbent core. The pledget further includes a three-dimensional apertured film mounted to the airlaid material, which engages the coverstock. The absorbent core is configured to fold about the hourglass shape of the pledget and resist undesired deformity of the absorbent article. The coverstock includes adhesive-coated elastic members disposed adjacent the longitudinal sides. The longitudinal sides are folded about a backsheet to enclose the core and pledget.

9 Claims, 4 Drawing Sheets

U.S. PATENT DOCUMENTS

| | | | |
|---|---|---|---|
| 4,655,759 A | 4/1987 | Romans-Hess et al. | 604/385 R |
| 4,685,915 A | 8/1987 | Hasse et al. | 604/378 |
| 4,687,478 A | 8/1987 | Van Tilburg | 604/387 |
| 4,699,619 A | 10/1987 | Bernardin | 604/378 |
| 4,701,178 A | 10/1987 | Glaug et al. | 604/387 |
| RE32,649 E | 4/1988 | Brandt et al. | 604/368 |
| 4,770,657 A | 9/1988 | Ellis et al. | 604/385 A |
| 4,773,905 A | 9/1988 | Molee et al. | 604/378 |
| 4,801,494 A | 1/1989 | Datta et al. | 428/283 |
| D300,693 S | 4/1989 | Grasso | D5/53 |
| D301,061 S | 5/1989 | Ternström et al. | D24/50 |
| D301,375 S | 5/1989 | Ternström et al. | D24/50 |
| 4,828,874 A | 5/1989 | Hiraoka et al. | 427/53.1 |
| 4,892,534 A | 1/1990 | Datta et al. | 604/370 |
| 4,900,320 A | 2/1990 | McCoy | 604/387 |
| 4,936,839 A | 6/1990 | Molee et al. | 604/378 |
| 4,950,264 A | 8/1990 | Osborn, III | 604/385.1 |
| 5,009,653 A | 4/1991 | Osborn, III | 604/385.1 |
| 5,019,062 A * | 5/1991 | Ryan et al. | 604/359 |
| 5,032,121 A | 7/1991 | Mokry | 604/385.2 |
| 5,047,023 A | 9/1991 | Berg | 604/368 |
| 5,074,856 A | 12/1991 | Coe et al. | 604/385.1 |
| 5,087,254 A | 2/1992 | Davis et al. | 604/386 |
| 5,092,860 A | 3/1992 | Pigneul | 604/380 |
| 5,147,343 A | 9/1992 | Kellenberger | 604/368 |
| 5,211,641 A | 5/1993 | Roos et al. | 604/385.1 |
| 5,248,309 A | 9/1993 | Serbiak et al. | 604/368 |
| 5,267,992 A | 12/1993 | Van Tilburg | 604/387 |
| 5,281,208 A | 1/1994 | Thompson et al. | 604/378 |
| 5,281,209 A | 1/1994 | Osborn, III et al. | 604/385.1 |
| 5,324,278 A | 6/1994 | Visscher et al. | 604/385.1 |
| 5,334,176 A | 8/1994 | Buenger et al. | 604/367 |
| 5,348,547 A | 9/1994 | Payne et al. | 604/378 |
| 5,354,400 A | 10/1994 | Lavash et al. | 156/227 |
| 5,356,403 A | 10/1994 | Faulks et al. | 604/378 |
| 5,364,382 A * | 11/1994 | Latimer et al. | 604/378 |
| 5,374,260 A | 12/1994 | Lemay et al. | 604/378 |
| 5,389,094 A | 2/1995 | Lavash et al. | 604/385.2 |
| 5,399,175 A | 3/1995 | Glaug et al. | 604/385.1 |
| 5,401,267 A | 3/1995 | Couture-Dorschner et al. | 604/384 |
| 5,413,568 A | 5/1995 | Roach et al. | 604/358 |
| 5,429,630 A | 7/1995 | Beal et al. | 604/385.1 |
| 5,460,623 A | 10/1995 | Emenaker et al. | 604/368 |
| 5,462,166 A | 10/1995 | Minton et al. | 206/440 |
| 5,466,232 A | 11/1995 | Cadieux et al. | 604/378 |
| 5,484,430 A | 1/1996 | Osborn, III | 604/385.1 |
| 5,489,283 A | 2/1996 | Van Tillburg | 604/387 |
| 5,490,846 A | 2/1996 | Ellis et al. | 604/366 |
| 5,509,914 A | 4/1996 | Osborn, III | 604/368 |
| 5,518,801 A | 5/1996 | Chappell et al. | 428/152 |
| 5,558,655 A | 9/1996 | Jezzi et al. | 604/378 |
| 5,562,645 A | 10/1996 | Tanzer et al. | 604/367 |
| 5,562,650 A | 10/1996 | Everett et al. | 604/378 |
| 5,569,231 A | 10/1996 | Emenaker et al. | 604/385.1 |
| 5,591,146 A | 1/1997 | Hasse | 604/359 |
| 5,591,149 A | 1/1997 | Cree et al. | 604/378 |
| 5,591,150 A | 1/1997 | Olsen et al. | 604/385.1 |
| H1634 H * | 2/1997 | Oetjen et al. | 604/385.23 |
| 5,601,542 A | 2/1997 | Melius et al. | 604/368 |
| 5,607,414 A | 3/1997 | Richards et al. | 604/378 |
| 5,607,415 A | 3/1997 | Datta et al. | 604/385.1 |
| 5,609,588 A | 3/1997 | DiPalma et al. | 604/369 |
| 5,620,430 A | 4/1997 | Bamber | 604/385.2 |
| 5,626,572 A | 5/1997 | Ahr et al. | 604/385.1 |
| 5,649,916 A | 7/1997 | DiPalma et al. | 604/378 |
| 5,665,452 A | 9/1997 | Langdon et al. | 428/131 |
| 5,674,214 A | 10/1997 | Visscher et al. | 604/385.1 |
| 5,681,300 A | 10/1997 | Ahr et al. | 604/367 |
| 5,681,303 A | 10/1997 | Mills et al. | 604/385.2 |
| D387,158 S | 12/1997 | Unger et al. | D24/124 |
| 5,704,930 A | 1/1998 | Lavash et al. | 604/385.2 |
| 5,713,883 A | 2/1998 | Hsieh | 604/385.1 |
| 5,716,349 A | 2/1998 | Taylor et al. | 604/385.1 |
| 5,728,084 A | 3/1998 | Palumbo et al. | 604/378 |
| 5,792,130 A | 8/1998 | Widlund et al. | 604/385.1 |
| 5,797,894 A | 8/1998 | Cadieux et al. | 604/378 |
| 5,800,654 A | 9/1998 | Davis et al. | 156/227 |
| 5,810,796 A | 9/1998 | Kimura et al. | 604/365 |
| D399,310 S | 10/1998 | Lynard et al. | D24/125 |
| D399,953 S | 10/1998 | Kollner | D24/125 |
| 5,827,255 A | 10/1998 | Crainic | 604/378 |
| 5,830,296 A | 11/1998 | Emenaker et al. | 156/219 |
| D403,765 S | 1/1999 | Brown et al. | D24/125 |
| 5,921,975 A | 7/1999 | Suzuki et al. | 604/385.2 |
| 5,947,945 A * | 9/1999 | Cree et al. | 604/368 |
| 6,004,893 A | 12/1999 | Van Tilburg | 442/381 |
| 6,042,575 A | 3/2000 | Osborn, III et al. | 604/387 |
| 6,059,710 A | 5/2000 | Rajala et al. | 493/346 |
| 6,068,619 A | 5/2000 | Hamajima et al. | 604/378 |
| 6,074,333 A | 6/2000 | Rajala et al. | 493/346 |
| 6,087,551 A | 7/2000 | Pereira | 604/367 |
| 6,103,953 A | 8/2000 | Cree et al. | 604/365 |
| D430,665 S | 9/2000 | Kirkbride et al. | D24/125 |
| 6,118,042 A | 9/2000 | Palumbo | 604/368 |
| D432,649 S | 10/2000 | Brown et al. | D24/125 |
| 6,172,276 B1 | 1/2001 | Hetzler et al. | 604/378 |
| 6,221,460 B1 | 4/2001 | Weber et al. | 428/131 |
| 6,231,556 B1 | 5/2001 | Osborn, III | 604/385.1 |
| 6,278,037 B1 | 8/2001 | Schmidt et al. | 604/369 |
| 6,306,123 B1 | 10/2001 | Salerno et al. | 604/385.31 |
| 6,326,525 B1 | 12/2001 | Hamajima et al. | 604/378 |
| 6,328,723 B1 | 12/2001 | Burns, Jr. et al. | 604/385.22 |
| 6,465,710 B1 | 10/2002 | Annergren et al. | 604/368 |
| 6,524,290 B2 | 2/2003 | Motta et al. | 604/385.01 |
| 6,605,752 B2 | 8/2003 | Magnusson et al. | 604/379 |
| 6,620,144 B1 * | 9/2003 | Glasgow et al. | 604/385.17 |
| 6,738,735 B1 | 5/2004 | Sherrod et al. | 703/2 |
| 6,740,069 B2 | 5/2004 | Drevik | 604/385.01 |
| 6,790,202 B2 | 9/2004 | Klemp et al. | 604/385.01 |
| 6,824,534 B2 | 11/2004 | Mishima et al. | 604/385.01 |
| 2002/0115971 A1 | 8/2002 | Holmes et al. | |
| 2002/0177830 A1 | 11/2002 | Fernandez-Kleinlein et al. | |

FOREIGN PATENT DOCUMENTS

| | | |
|---|---|---|
| WO | WO 91/11162 | 8/1991 |
| WO | WO 94/28838 | 12/1994 |
| WO | WO 98/43684 | 10/1998 |

* cited by examiner

MULTIPLE LAYER ABSORBENT ARTICLE

BACKGROUND

1. Technical Field

The present disclosure generally relates to disposable absorbent articles, and more particularly, to disposable absorbent articles having a multiple layer absorbent whereby the layers cooperate to prevent undesired deformity.

2. Background of the Related Art

Absorbent articles such as, for example, disposable diapers, adult incontinent pads, sanitary napkins, pantiliners, incontinent garments, etc. are generally worn, in cooperation with garments and disposed against a body surface, etc., by infants or adult incontinent individuals. The absorbent article is employed to collect, absorb, etc. body fluid discharge, such as, for example, blood, menses, urine, aqueous body fluids, mucus, cellular debris, etc. For example, the absorbent article may be disposed between the legs of an individual adjacent a crotch area. The absorbent article is positioned with a garment and drawn into engagement with a body surface of the crotch area to collect fluid discharge.

As is known, absorbent articles typically include a fluid permeable coverstock for engaging the body surface, a fluid impermeable back sheet and an absorbent core supported therebetween. The back sheet serves as a moisture barrier to prevent fluid leakage to the garment. The absorbent core usually includes a liquid retention material that faces the body surface. The absorbent core can include loosely formed cellulosic fibers, such as wood pulp, for acquiring and storing fluid discharge.

The absorbent core absorbs fluid discharge and with regard to adult absorbent articles, such as, incontinent pads, are made fairly thick to handle large quantities of fluid, such as urine. The absorbent cores, however, can be unseemly due to their size and bulk. One of the disadvantages of these absorbent articles is the thick, diaper-like appearance which may be embarrassing to an adult wearer.

More recently, to overcome bulkiness, other absorbent articles, particularly feminine pads, sanitary napkins, pantiliners, incontinent garments, etc., are manufactured as long, narrow and relatively flat. These absorbent articles are designed to be worn close against the body surface and held in place by an undergarment. Some of these designs, however, have a tendency to deform undesirably by, for example, bunching, roping, wrinkling, etc. upon engagement with the body surface. Undesired deformity of the absorbent article may result in leakage of fluid discharge.

Fluid discharge leakage typically results, not from oversaturation of the absorbent core, but from pooled fluid discharge run off. To wit, during a fluid discharge, such as a void, it is common for urine to deposit onto the coverstock to form a pool before it penetrates the absorbent core. If the absorbent article is undesirably deformed and pooling occurs, urine will not be absorbed because the core is bunched. Thus, fluid run off occurs and premature leakage from the absorbent article results.

Attempts have been made to provide improved fitting absorbent articles. Some designs provide arcuate shaped pads incorporating elastic elements along longitudinal sides thereof. See, e.g., U.S. Pat. Nos. 4,701,177 and 4,770,657. Other designs attempt to prevent leakage by utilizing multiple layer top sheet, absorbent core, etc. arrangements structured to absorb run off. See, e.g., U.S. Pat. Nos. 5,211,641, 5,792,130, 5,558,655, 5,599,334 and 5,913,850. Designs of this type, however, do not address product flexibility for causing desired deformity to facilitate fluid management. These prior art designs may not adequately prevent undesirable deformity which can impede absorbency performance. Undesired product deformity alters the desired shape of the absorbent article and causes premature leakage.

It would therefore be desirable to overcome the disadvantages and drawbacks of the prior art by providing an absorbent article including a multiple layer absorbent whereby the layers cooperate to prevent undesired deformity and facilitate desired deformity to improve absorbency performance. It is contemplated that the absorbent article includes an absorbent pledget with increased stiffness to provide structural stability. It is further contemplated that the absorbent article conforms to the contour of a body surface and allows for quick dispersal of fluid discharge.

SUMMARY

Accordingly, an absorbent article is disclosed which includes a multiple layer absorbent whereby the layers cooperate to prevent undesired deformity and facilitate desired deformity, such as, for example, conforming to the contour of a body surface to improve absorbency performance. The absorbent article desirably includes an absorbent pledget with increased stiffness to provide structural stability. Most desirably, the absorbent article allows for the product to conform into a three directional, cup-shaped configuration, which creates barrier walls to contain full flowing fluid from leaking out of the pad, and then provides the quick dispersal of fluid discharge through advantageous fluid management. The absorbent pledget acts like a "backbone" in the product, allowing the softer and more flexible absorbent core underneath it to fold around it in an upward direction when placed under elastic tension along the sides.

Objects and advantages of the present disclosure are set forth in part herein and in part will be obvious therefrom, or may be learned by practice of the present disclosure which is realized and attained by the instrumentalities and combinations pointed out in the appended claims for the devices and methods of the present disclosure consisting of its constituent parts, constructions, arrangements, combinations, steps and improvements herein shown and described.

The absorbent article, in one particular embodiment in accordance with the principles of the present disclosure includes a dual absorbent core system having an airlaid composite on top and a pulp/super absorbent polymer material core on the bottom. The absorbent article also includes a three dimensional apertured film as acquisition layer, cloth-like backsheet, soft elastic side gathers, soft/comfortable coverstock, pressure sensitive adhesive track(s) and release paper. The three dimensional apertured film is adhered to the airlaid composite, with the male side facing the airlaid. The airlaid composite and apertured three dimensional film layer are cut into an hour-glass/contoured pattern configuration. This is narrower in width and shorter in length relative to the pulp/super absorbent polymer material core layer underneath. This design has a lower basis weight and is stiffer in structural stability relative to the pulp/super absorbent polymer material core. The pulp/super absorbent polymer material core is thin and flexible for easy bending when subjected to forces via bodily movement or elastic retraction.

Alternately, the pulp/super absorbent polymer material core may be fabricated from foam with super absorbent polymer material, tissue with super absorbent polymer material, nonwoven with super absorbent polymer material, etc. as well as conventional pulp fluff and super absorbent particulate substrates that may be tissue wrapped. The coverstock is soft and somewhat lofty to provide improved softness and comfort. The elastic members or strands are directly coated with adhesive to minimize stiffness associated with high adhesive add-ons. They are adhered to the coverstock, which is folded over in a c-fold configuration. The clothlike fluid-impervious barrier extends beyond the longitudinal side edges of the pulp/super absorbent polymer material absorbent core without contacting the elastic members. This configuration advantageously provides softer elastic gathers because less material is retracted.

The clothlike fluid-impervious barrier can be fabricated from a poly-laminate (nonwoven & poly), breathable poly-laminate (micropororous film & nonwoven), high basis weight SMS or SMMS with slot-coat adhesive, etc. The positioning adhesive may include one or more tracks that are intermittently registered on the nonwoven side of the clothlike backsheet. Hot melt adhesive can be used for the positioning adhesive, utilizing tactifying materials such as styrene-butadiene-styrene (SBS), styrene-isoprene-styrene (SIS), SIS/SBS, styrene ethylene/butylenes styrene (SEBS) formulations. A cut and placed release paper is attached over the positioning adhesive. Printed paper with silicone coating on one side, facing the positioning adhesive, may be used. A printed polylaminate with silicone coating can also be used.

The presently disclosed absorbent article provides a shape and composition of the combined airlaid composite and three dimensional apertured film acquisition layer. This configuration fits in a crotch area of an individual, providing comfort during use. The central section can be narrower than either one or both outer ends of the absorbent core composite. This allows for numerous shapes and dimensional configurations to fit in the crotch area when the thighs of the individual are in contact. The airlaid composite can be stiffer than the other components of the absorbent article, providing a backbone to reduce absorbent core bunching and roping. To further facilitate fitting of the airlaid composite, the composite can be reduced in cross-sectional width.

The pulp/super absorbent polymer material absorbent core may be thinner and constructed of lower basis weight absorbent material designed to underly the composite. The pulp/super absorbent polymer material is larger in cross-sectional width and in longitudinal length. This design advantageously absorbs urine run-off from the airlaid composite and can be easily conformed into a cup-shape configuration with the retractive forces of elastics under tension. The pulp super absorbent polymer material absorbent core is highly flexible, resilient and has good integrity both in the dry and wet states. Alternatively, the airlaid composite may be disposed under the absorbent core material. The airlaid composite and absorbent core of the dual absorbent layers can differ by basis weight, stiffness, surface area, pulp/super absorbent polymer material blends, density, shape, material make-up and thickness to achieve the desired advantages of the present disclosure.

To maximize absorbency performance, elastic members are elongated at both sides of the product creating a "bucket-like" configuration around the absorbent core. This reduces premature leakage associated with liquid run-off and pooling when the absorbent is over-saturated or is subjected to high void levels. The three dimensional apertured film reduces fluid discharge from coming back through the coverstock when subjected to pressure and over-saturation (rewet). Lower rewet values promote skin wellness and reduced irritation.

To maximize comfort during use, the coverstock is constructed of softer fibers, such as, for example, bi-component fibers that are through-air bonded (no harsh point-bonds), etc. The bi-component fiber may consist of a polypropylene or polyester inner core, promoting strength and a polyethylene outer sheath, promoting softness and ability to thermal bond. The backsheet material can have a garment facing nonwoven layer which contacts a body surface adjacent the elastic gathers.

In another embodiment, the absorbent articles provides a fluid permeable body facing surface and an absorbent core having a body facing side. An absorbent pledget is adhered to the body facing side of the absorbent core and is disposed between the absorbent core and the body facing surface. The pledget has a greater structural stiffness and a reduced surface area relative to the absorbent core. The pledget is configured to fit a human anatomy.

In another alternate embodiment, the absorbent article has a fluid permeable coverstock configured to engage a body surface and defining longitudinal sides. The coverstock includes a bi-component fiber having a polypropylene or polyester inner core and a polyethylene outer sheath. An absorbent core of the absorbent article has a body facing side, an opposing side and extends longitudinally along the absorbent article. The absorbent core has arcuate outer ends and includes wood pulp and superabsorbent polymer materials. An hourglass shaped absorbent pledget is disposed between the absorbent core and the coverstock. The pledget includes airlaid material adhered to the body facing side of the absorbent core. The pledget further includes a three dimensional apertured acquisition film mounted to the airlaid material which engages the coverstock. The pledget has a greater structural stiffness and reduced surface area relative to the absorbent core. The absorbent core is configured to fold about the hourglass shape of the pledget and resist undesired deformity of the absorbent article. The coverstock includes adhesive coated elastic members disposed adjacent the longitudinal sides. The longitudinal sides are folded about a polylaminate backsheet to enclose the absorbent core and pledget.

In another alternate embodiment, the absorbent pledget has structure means for absorbing fluid discharge and resisting undesired deformation of the absorbent core.

BRIEF DESCRIPTION OF THE DRAWINGS

The objects and features of the present disclosure are set forth with particularity in the appended claims. The present disclosure, as to its organization and manner of operation, together with further objectives and advantages may be understood by reference to the following description, taken in connection with the accompanying drawings, in which:

DETAILED DESCRIPTION OF EXEMPLARY EMBODIMENTS

The exemplary embodiments of the absorbent article and methods of use disclosed are discussed in terms of fluid absorbent articles, and more particularly, in terms of an absorbent core having a multiple layer configuration whereby the layers cooperate to provide maximum protection and comfort to an individual wearing the absorbent article. It is contemplated that the absorbent article, in accordance with the principals of the present disclosure, prevents undesired product deformity, such as, for example, roping, bunching, breaks, wrinkling, etc. and facilitates desired deformity, such as, for example, conforming to the contour of a body surface, etc. to improve absorbency. The presently disclosed absorbent article thereby avoids premature leakage, overflow, etc., of fluid discharge, such as, for example, blood, menses, urine, aqueous body fluids, mucus, cellular debris, etc. It is contemplated that the absorbent article may be employed with disposable diapers, adult incontinent pads, feminine pads, sanitary napkins, pantiliners, incontinent garments, etc. It is further contemplated that the present disclosure can also be used with bedding and furniture underpads, wound dressings, etc.

In the discussion that follows, the term "body facing surface" refers to a portion of a structure that is oriented towards a body surface, and the "garment facing surface" refers to a portion of the structure which is oriented towards a garment and is typically opposing the body facing surface and may be referred to as such. As used herein, the term "body surface" refers to a portion of an individual's body that the absorbent article is disposed with for collecting, absorbing, etc. fluid discharge from the individual.

The following discussion includes a description of the absorbent article, followed by a description of the method of use therefor in accordance with the present disclosure. Reference will now be made in detail to the exemplary embodiments of the disclosure, which are illustrated in the accompanying figures.

Figure 1:
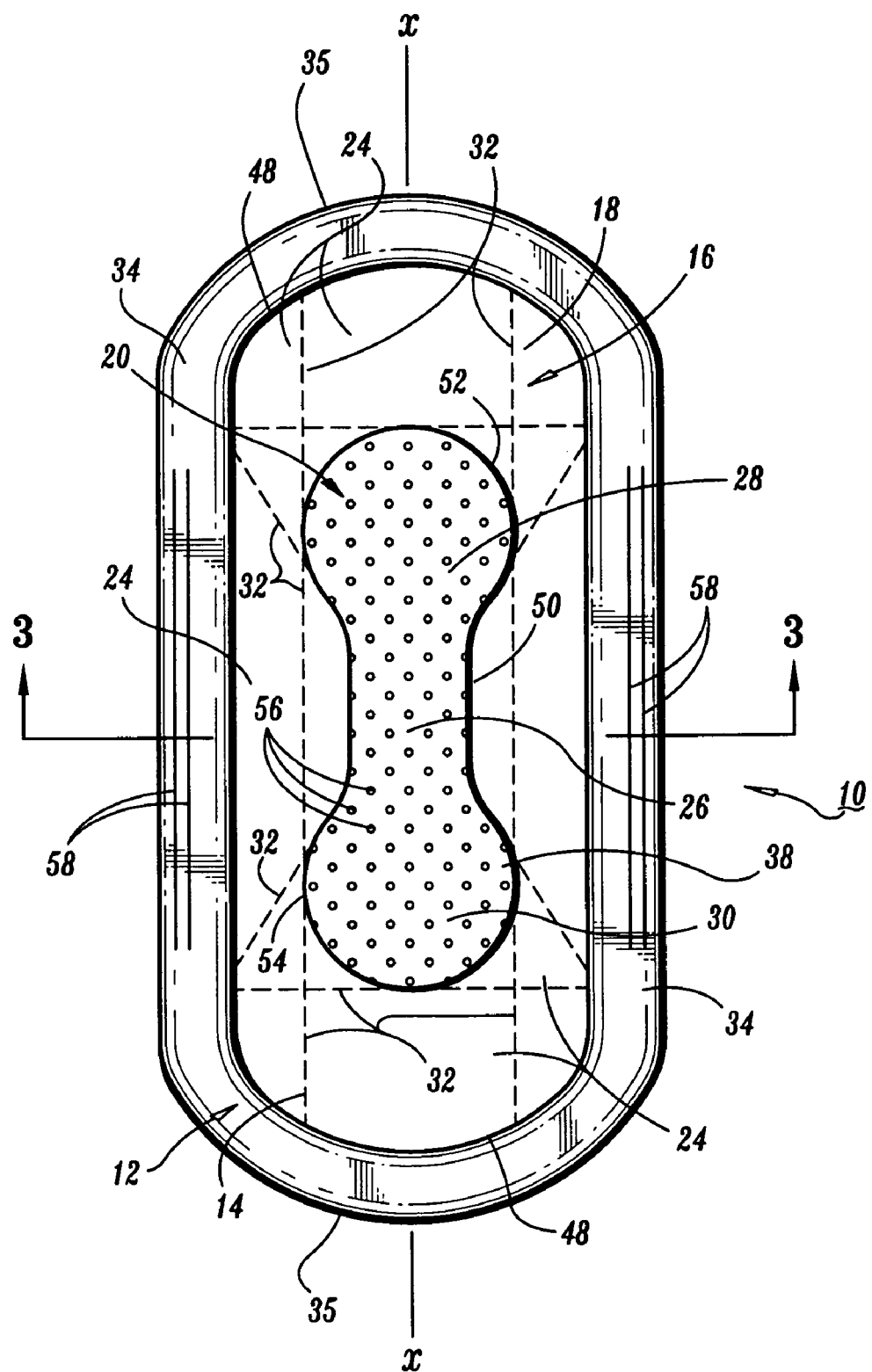
FIG. 1 is a top plan view of one particular embodiment of an absorbent article in accordance with the principals of the present disclosure.
Figure 2:
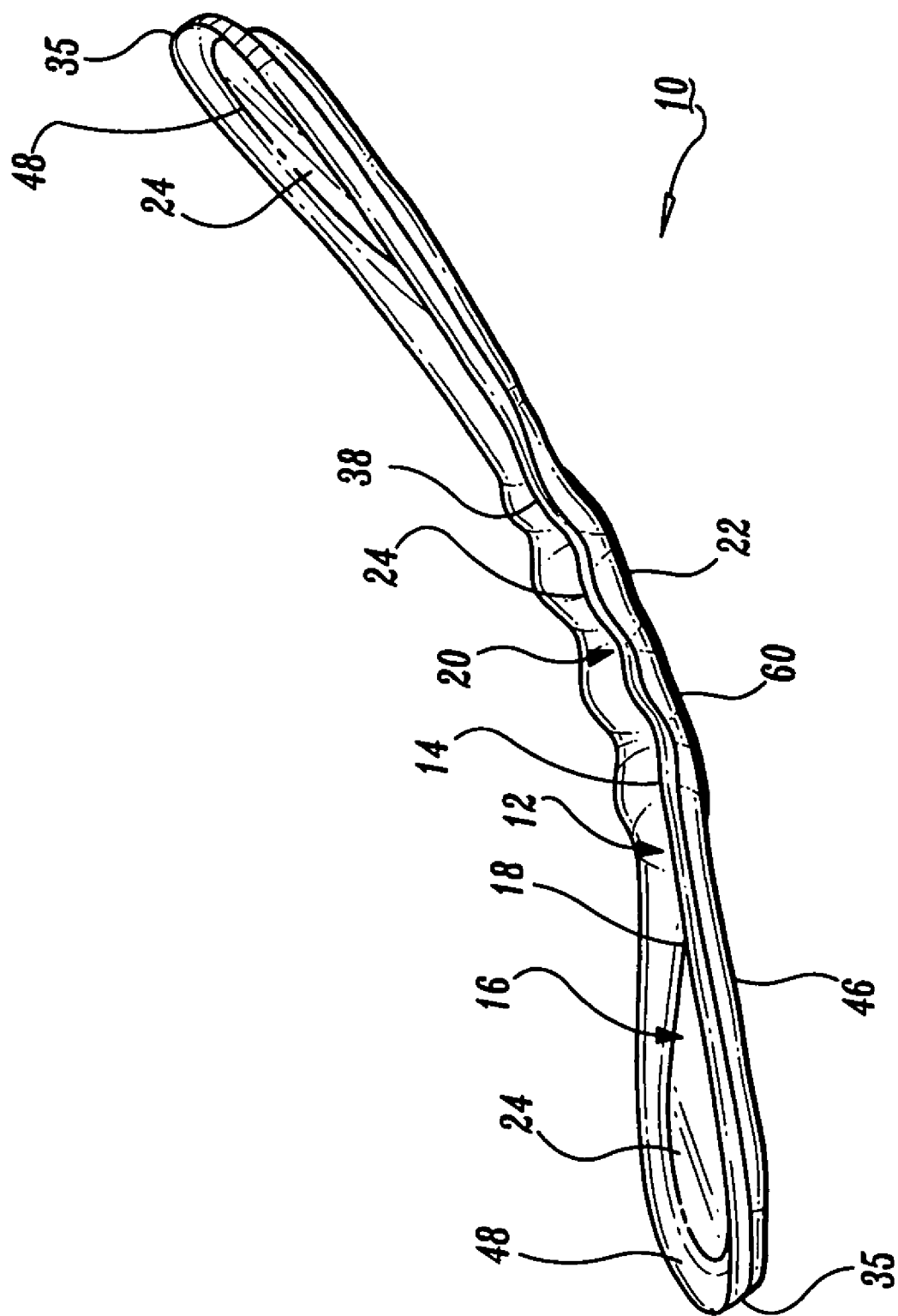
FIG. 2 is a side cross-sectional view of the absorbent article shown in FIG. 1.
Figure 3:
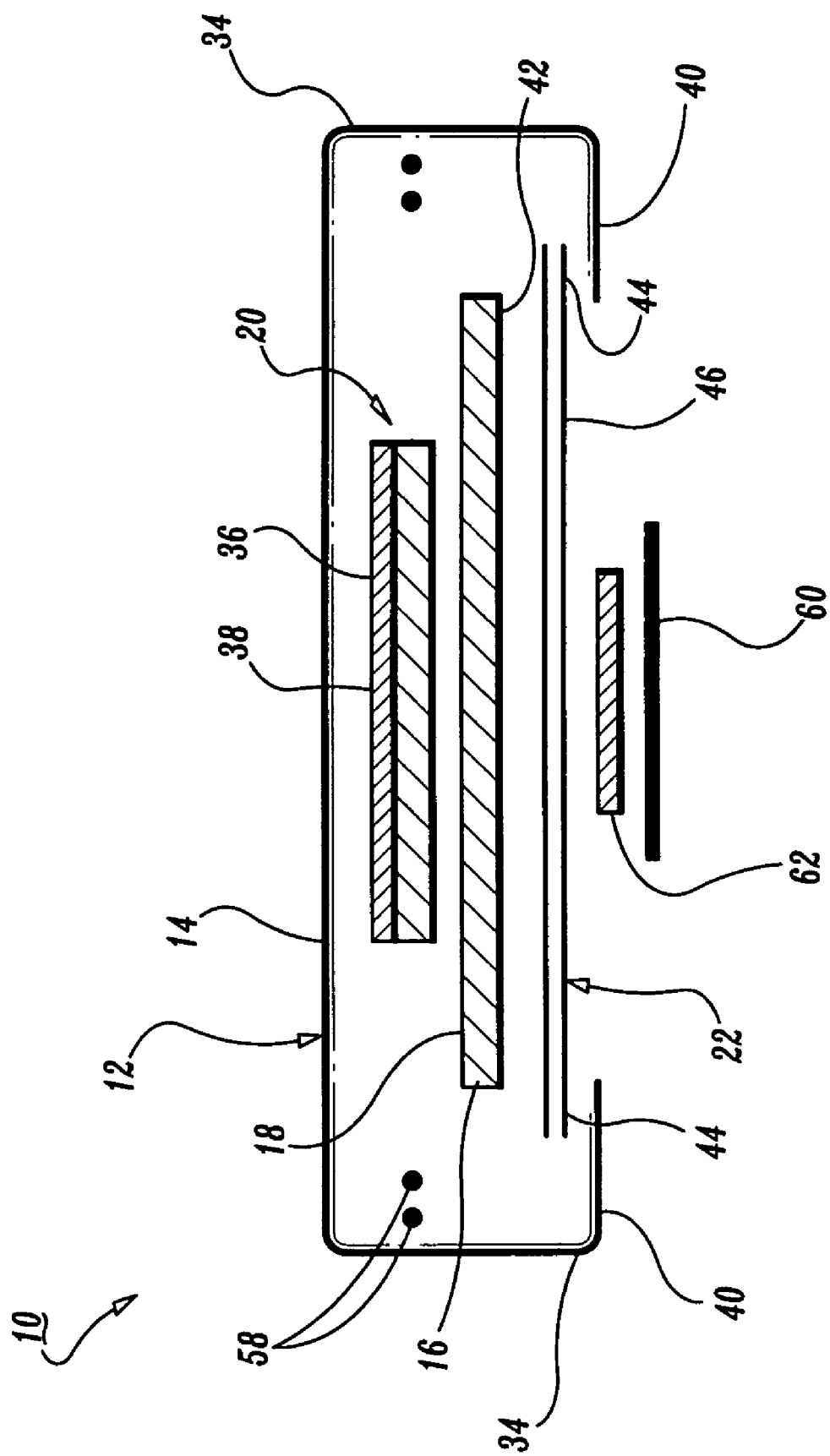
FIG. 3 is a side perspective view of the absorbent article shown in FIG. 1.

Turning now to the figures, wherein like components are designated by like reference numerals throughout the several views. Referring initially to FIGS. 1–3, there is illustrated an absorbent article 10, constructed in accordance with the principals of the present disclosure, including a fluid permeable top sheet such as, for example, coverstock 12 having a body facing surface 14. Absorbent article 10 further includes an absorbent core 16 having a body facing side 18.

An absorbent pledget 20 is adhered to body facing side 18 and disposed between absorbent core 16 and body facing surface 14 of coverstock 12. Absorbent pledget 20 has a greater structural stiffness and a reduced surface area relative to absorbent core 16. Absorbent core 16 and absorbent pledget 20 are supported between coverstock 12 and a fluid impermeable back sheet 22. It is contemplated that absorbent article 10 may include one or a plurality of absorbent layers, absorbent pledgets, top sheets and/or back sheets. It is further contemplated that the absorbent core(s) and pledget(s) may be relatively disposed such as, for example, alternately layered, core disposed between pledget and coverstock, etc., in accordance with the principles of the present disclosure.

Absorbent pledget 20 has a greater structural stiffness and a reduced surface area relative to absorbent core 16 such that absorbent core 16 is configured to desirably deform by, such as, for example, folding about absorbent pledget 20, conforming to the contour of a body surface, etc. It is contemplated that such desired deformation forms absorbent compartments 24 (shown in phantom in FIG. 1), which conform to a body surface to absorb fluid discharge as will be discussed below, and resists undesired deformity of absorbent article 10. Absorbent article 10 is advantageously configured to prevent undesired product deformity, improving absorbency performance, and thereby avoiding premature leakage, overflow, etc. due to fluid discharge. Most advantageously, absorbent article 10 conforms to the contour of a body surface and allows for quick dispersal of fluid discharge through its fluid management features, as discussed.

Absorbent core 16 and absorbent pledget 20 are disposed along a longitudinal length of absorbent article 10. As shown in FIG. 1, absorbent article 10 can be flattened to a planar configuration to define a longitudinal axis x. It is envisioned that absorbent core 16 and absorbent pledget 20 may be alternatively disposed relative to longitudinal axis x, such as, for example, transverse, offset, etc. During use, such as, for example, during bodily movement or elastic retraction, absorbent core 16 and absorbent pledget 20 cooperate to define compartments 24 via desired deformity of absorbent core 10. This configuration facilitates desired deformation and prevents undesired deformity of absorbent article 10 due to higher relative stiffness which provides a backbone-like structure for absorbent article 10.

The configuration and dimension of compartments 24 are variously defined according to the specifications of absorbent core 16 and absorbent pledget 20. As shown in FIG. 1 (in phantom), absorbent core 16 desirably deforms about the hourglass configuration of pledget 20 depending on bodily movement, size of an individual, etc. For example, multiple compartments 24 can be formed, although not necessarily simultaneously. It is contemplated, however, that compartments 24 may be formed simultaneously. The formation of a particular compartment 24 or region of compartments 24 may depend, for example, on the direction of bodily movement, etc.

The boundaries of compartments 24 are defined by, upon desired deformity, channels 32 which are configured to facilitate flexibility of absorbent article 10 relative to a body surface (not shown). It is contemplated that channels 32 advantageously distribute fluid flow toward longitudinal sides 34 of absorbent article 10 to utilize more absorbent media of absorbent core 16, preventing leakage. It is further contemplated that the formation of channels 32 facilitates conforming of absorbent article 10 to the contour of the body surface and allows for quick dispersal of fluid discharge. The orientation of channels 32 is determined by the configuration of compartments 24.

Absorbent pledget 20 has a lower basis weight and higher density for stiffer structural stability versus the higher basis weight of absorbent core 16. Absorbent core 16 is more flexible relative to absorbent pledget 20 such that absorbent core 16 conforms to a bucket or cup shape, as will be discussed. This configuration advantageously provides comfort and improved absorbency performance. This is due to absorbent article 10 features including desired deformity and resistance to roping, bunching, etc.

Absorbent article 10 fits and is contoured with a crotch area of an individual to provide comfort during use. For example, absorbent pledget 20 has a narrow central section 26 and outer ends 28, 30, discussed in detail below, to provide improved fit with the crotch area. It is envisioned that only one of outer ends 28, 30 have a greater width than central section 26 or alternatively that section 26 and ends 28, 30 have similar widths. Absorbent pledget 20 has a smaller surface area and is adhered to absorbent core 16 which has a larger surface area. It is contemplated that the larger surface area of absorbent core 16 facilitates absorption of fluid discharge run-off from absorbent pledget 20.

Absorbent article 10 is contemplated for fluid retention of discharged body fluids. More particularly, absorbent article 10 is envisioned to be a disposable absorbency device employing, among other things, absorbency and body conforming features to prevent leakage and overflow of fluids, as well as resistance to undesired deformity. The above advantages, among others, realized from the present disclosure are attained by absorbent article 10, which is flexibly conforming to a body surface, as discussed herein. These features of the present disclosure advantageously facilitate fluid retention of discharged fluids and prevent consequent overflow.

Coverstock 12 is disposed adjacent to a body facing surface 36 of absorbent pledget 20 and is configured to be worn against the body surface of an individual. Body facing surface 36 includes an acquisition film layer 38, discussed below, adhered thereto.

Acquisition film layer 38 is configured to directly engage coverstock 12 for absorption and transmission of fluid discharge to portions of absorbent article 10, including absorbent pledget 20 and absorbent core 16. Coverstock 12 engages absorbent core 16 and may engage other portions of absorbent pledget 20, according to the particular absorbency application in accordance with the present disclosure. In use, coverstock 12 is body fluid permeable, resilient, relatively non-absorbing and configured to facilitate directing fluid discharge to absorbent pledget 20 and absorbent core 16. Consequently, coverstock 12 is easily permeated by fluid discharge. Further, coverstock 12 retains minimal or no fluid in its structure to provide a relatively dry surface adjacent the body surface. It is also designed for comfort and conformability to an individual. It is envisioned that coverstock 12 is fabricated from a bi-component fiber and through-air bonded. For example, the bi-component fiber may include a polypropylene or polyester inner core for strength and a polyethylene sheath for softness and the ability to thermally bond. It is contemplated that the coverstock material used is soft and at least partially lofty.

Coverstock 12 can be fabricated from a woven, non-woven, apertured film, natural or synthetic material easily penetrated by fluid discharge. Coverstock 12 is a single sheet of material having a width sufficient to overlay longitudinal sides 34 and arcuate ends 35 adjacent its longitudinal ends. Ends 35 may have other geometric configurations. As shown in FIG. 3, coverstock 12 extends laterally in a c-fold configuration. This configuration cooperates with fluid impermeable back sheet 22 to enclose the components of absorbent article 10. It is envisioned that top sheet 12 may include multiple layers.

Coverstock 12 forms outer edge 40 sealed with back sheet 22 to fully enclose the components of absorbent article 10. It is contemplated that coverstock 12 may be disposed over only a portion of absorbent article 10. Coverstock 12 may be fabricated from fibers or filaments of thermoplastic polymers, such as, for example, polyethylene, polypropylene, polyester, etc. Coverstock 12 may also be made from other materials which allow the ready passage of fluid through to absorbent pledget 20 and absorbent core 16, as is known to one skilled in the art. This includes apertured films, apertured nonwovens, rayon fibers, bi-component fibers, tissue, etc.

Back sheet 22 is disposed adjacent to a garment facing surface 42 of absorbent core 16 and extends to an edge 44 for sealing engagement with outer edge 40. Back sheet 22 generally faces away from the body surface and towards an undergarment worn by an individual. Back sheet 22 may permit passage of air and vapor from absorbent article 10 while preventing passage of fluid discharge therefrom. Alternatively, back sheet 22 may be completely fluid and vapor impervious. A garment facing side 46 of back sheet 22 has a cloth-like texture and is non-woven. Materials of fabrication for back sheet 22 can include fluid impermeable materials such as, for example, polylaminates, high basis weight SMS, SMMS with slot coat adhesive, polymeric films such as polyethylene, polypropylene, polyester, cellophane, etc. or a bi-component film such as ethel-vinyl-acetate and polyethelyne coextruded film. A treated material may also be used such as impregnated fluid repellent paper or a non-woven fabric. Other materials, however, may be used as is known to one skilled in the art.

Outer edges 40, 44 may be joined by pressure sensitive adhesives, heat sensitive adhesives, ultrasonics or by other known joining applications which prevent fluid discharge flow beyond outer edges 40, 44 and, consequently, from absorbent article 10.

The sealing engagement of outer edges 40, 44 extends continuously along the longitudinal length of absorbent article 10, adjacent longitudinal sides 34. It is contemplated, however, that the sealing engagement may be discontinuous, staggered, etc. It is envisioned that outer edges 40, 44 may extend outwardly various lengths or, alternatively, absorbent article 10 may not include edges 40, 44.

Absorbent core 16 is disposed longitudinally along absorbent article 10 to facilitate placement adjacent a body surface. The longitudinal configuration of absorbent article 10 permits placement between an individuals' thigh area and can be drawn up to cover the crotch area. At its outer ends, absorbent core 16 has arcuate edges 48 aligned with arcuate edges 35 of coverstock 12. Edges 35, 48 are also flexible for conforming to the body surface. It is envisioned that absorbent article 10 and absorbent core 16 individually, may be manufactured in various configurations and dimensions, such as, for example, rectangular, oval, hourglass, etc. Absorbent core 16 is soft and configured for comfort to an individual.

Absorbent core 16 is fabricated from a pulp/super absorbent polymer material. This forms a thin and flexible layer to facilitate desired deformity about absorbent pledget 20 upon application of forces, such as, for example, body movement, elastic retraction, etc. Absorbent core 16 has a higher basis weight and lower density than absorbent pledget 20 and is highly flexible, resilient, and has improved integrity in both dry and wet conditions. Absorbent core 16 basis weight can range from 50 to 1000 gsm, depending on the size of absorbent article 10. Absorbent article 10 may be fabricated in a variety of sizes and absorbency levels. Absorbent core 16 has a substantially rectangular configuration with rounded ends. However, other shapes are envisioned.

In addition, the surface area of absorbent core 16 is variable depending on the size and absorbency level of absorbent article 10. The surface area of absorbent core 16 may range from 100 to 800 cm$^2$. The density of absorbent core 16 is approximately 0.08 g/cc and the density of absorbent pledget 20 is approximately 0.10 g/cc. The blend of absorbent core 16 preferably includes pulp (ranging from 55%–95%), superabsorbent particles (ranging from 5%–45%) and may be tissue wrapped. The blend of absorbent pledget 20 preferably includes pulp (approx. 65%), superabsorbent particles (approx. 25%) and binder fiber (approx. 10%). The binder fiber is bicomponent fiber with polyester on inner core and polyethylene on the outer sheath. For illustrative purposes only, some possible sizes and absorbency levels of absorbent article 10 are:

| Item | Property | Units | Size 1 | | Size 2 | Size 3 | | Size 4 |
|---|---|---|---|---|---|---|---|---|
| Product | Area | cm² | 222.5 | 222.5 | 250 | 315 | 315 | 364 |
| | Capacity | gms | 140 | 175 | 280 | 320 | 370 | 420 |
| Absorbent | Area | cm² | 143 | 143 | 163 | 210 | 210 | 248 |
| Core | Basis Weight | gsm | 440 | 690 | 830 | 650 | 750 | 735 |
| | % Pulp | % | 67 | 79 | 68 | 62 | 60 | 63 |
| | % SAP | % | 33 | 21 | 32 | 38 | 40 | 37 |
| | Density | g/cc | multiple | multiple | multiple | multiple | multiple | multiple |
| | Capacity | grams | 120 | 155 | 253 | 300 | 330 | 370 |
| Pledget | Area | cm² | 83 | 83 | 99 | 130 | 130 | 163 |
| | Basis Weight | gsm | 250 | 250 | 250 | 250 | 250 | 250 |
| | % Pulp | % | 65 | 65 | 65 | 65 | 65 | 65 |
| | % SAP | % | 25 | 25 | 25 | 25 | 25 | 25 |
| | % bico fibers/binder | % | 10 | 10 | 10 | 10 | 10 | 10 |
| | Density | g/cc | 0.1 | 0.1 | 0.1 | 0.1 | 0.1 | 0.1 |
| | Capacity | grams | 20 | 20 | 30 | 40 | 40 | 50 |

Note that absorbent pledget 20 in the table above was kept constant in terms of basis weight and material make-up, for simplification. However, other basis weights and materials may be used for each option, according to the particular requirements of an absorbent article application.

Materials for absorbent core 16 capable of absorbing and retaining fluid discharge may be used, such as, for example, a hydrophilic material such as cellulose fibers, wood pulp, re-generated cellulose, rayon, viscose, cotton fibers, or a blend of pulp and other fibers or foam with super absorbent polymer material. Bulk of absorbent article 10 can be reduced by adding superabsorbent polymer materials, having high liquid retention properties such as, for example, hydrocolloidal material, cross-linked acrylete polmers, etc., according to the requirements of a particular absorbency application. In addition, super absorbent fibers could be used as well. Super absorbent polymer particles can be permeated, desirably in granular form, through absorbent core 16. It is contemplated that super absorbent polymer particles used are in the range of 3 to 8 grams, although other ranges are envisioned.

Body facing side 18 of absorbent core 16 may include one or more acquisition layers which aid in the transfer of fluid discharge to absorbent core 16. This layer may include a tissue layer embossed or adhered to absorbent core 16. Absorbent core 16 may also be chemically or physically modified. It is contemplated that the absorbent cores may include such materials in combination with other materials both natural and synthetic, such as airlaid materials, creeped cellulose wadding, melt blown polymers, tissue layers, tissue wraps, tissue laminates, foams, cellulose acetate, sponges, jelling material, etc.

Alternate designs are also envisioned whereby absorbent core 16 may have varying caliper zones, hydrophilic gradients, super absorbent gradients, low-density acquisition zones, multiple layers or structures, etc., according to the particular requirements of an absorbent article application.

Absorbent pledget 20 has an hourglass configuration extending longitudinally along absorbent article 10. Absorbent pledget 20 is ultimately positioned in the crotch area of an individual and may have other configurations for placement therewith. Central section 26 extends longitudinally along absorbent article 10 and includes opposing concave sides 50. Outer ends 28, 30 have arcuate surfaces 52, 54 respectively. Concave sides 50 and arcuate surfaces 52, 54 facilitate desired deformity of absorbent core 16 about absorbent pledget 20 to form compartments 24 defined by boundary channels 32. This configuration advantageously facilitates conformity to a body surface and prevents undesired deformity of absorbent article 10 to prevent fluid discharge leakage.

Concave sides 50 and surfaces 52, 54 may have various geometric configurations for conforming to a body surface and facilitating desired deformity of absorbent article 10. Compartments 24 contour to the conformity of a body surface such that fluid discharge distributed therethrough flows toward longitudinal sides 34. This facilitates employment of more of absorbent core material as needed before failure can occur due to leakage. Compartments 24 aid absorbent article 10 in achieving these advantages by moving with the body surface during wear thus, fluid discharge is quickly dispersed and effective fluid management is performed.

Absorbent pledget 20 is adhered to body facing side 18 of absorbent core 16 and is fabricated from an airlaid composite material. Absorbent pledget 20 is narrower in width, shorter in length, has a lower basis weight and is stiffer in structural stability relative to absorbent core 16. Absorbent pledget 20 includes a three dimensional acquisition film layer 38 adhered to body facing surface 36. Layer 38 includes apertures or cones 56 which facilitate fluid discharge flow to absorbent pledget 20. Thus, layer 38 manages, transports, accommodates and/or directs high volumes and high flow rates of fluid discharge to absorbent pledget 20. Layer 38 is configured to prevent fluid discharge from wetting through coverstock 12 when, for example, subjected to pressure, over-saturation (rewet). This advantageously reduces rewet to promote skin wellness and reduce irritation. It is contemplated that layer 38 can be a through air bonded web, a bi-component non-woven web, cellulosic fibers, etc. Layer 38 may be adhesively secured in place by any suitable construction adhesive for absorbent core applications. It is envisioned that absorbent pledget 20, including layer 38, is manufactured via die-cutting and registered although other fabrication methods known to one skilled in the art may be utilized.

Absorbent article 10 includes elastic members 58 disposed with longitudinal sides 34. Elastic members 58 are configured to desirably deform the planar configuration of absorbent article 10. This desirable deformation resiliently pulls ends 35, 48 toward each other relative to absorbent pledget 20. This resilient tendency of absorbent article 10 forms a cup or bucket shaped configuration, facilitated by absorbent pledget 20. Elastic members 58 form side gathers configured to wrap around and conform to the inner thigh area of an individual. Elastic members 58 are coated with adhesive and adhered to coverstock 12. This configuration minimizes stiffness. Elastic members 58 desirably do not contact backsheet 22. This advantageously reduces the amount of material retracted by elastic members 58, thereby softening the side gathers.

It is contemplated that varying lengths of elastic may be used. It is further contemplated that varying widths, individual strands or threads, round, square, or rectangular configurations, multiple strands grouped together, etc. may be used. The degree of elasticity, stiffness and flexibility of elastic members 58 may be altered according to the requirements of a particular absorbent article application. The side gathers of elastic members 58 may form a cuff-like shape about the thighs of an individual. The elastic members may be fabricated from any suitable material, such as, for example, synthetic or natural rubbers, such as heat sealable and heat shrinkable, latex, polyurethane, spandex, elastic foam, etc. It is contemplated that slot coating, spiral spray, meltblown, direct elastic coating or other adhesive applications may be used to secure elastic members 58 with coverstock 12.

Back sheet 22 is a moisture barrier and includes a release strip 60 affixed thereto. Release strip 60 fully covers the positioning adhesive 62 and acts as protection to keep it from becoming exposed prior to use. The positioning adhesive 62 fixes absorbent article 10 to the outer crotch portion of an undergarment (not shown). Release strip 60 includes silicone coating to allow easy removal of the release strip 60 from the positioning adhesive 62 when the absorbent article 10 is ready to be used. Positioning adhesive 62 may include one or more adhesive tracks, intermittently registered on garment facing side 46 of back sheet 22. A hot melt adhesive is used for positioning. It is envisioned that positioning adhesive 62 may include a pressure sensitive adhesive material such as, for example, a water based adhesive such as, acrylic adhesives, etc. It is further envisioned that rapid setting thermoplastic adhesives, two-sided adhesive tape, adhesives based on natural or synthetic rubbers, etc. may be used. It is contemplated that adhesive 62 may include alternative shapes such as lines, squares, circles, etc.

In use, absorbent article 10 is properly prepared and packaged for consumer application. The absorbent article 10 may be also be sterilized, if so desired. Release strip 60 is removed to expose positioning adhesive 62. Positioning adhesive 62 is brought into engaging contact with an undergarment of an individual (not shown) for attachment therewith. Absorbent article 10, with the undergarment, is disposed between the thighs of the individual. Ends 35, 48 of absorbent core 16 are oriented towards the front and the rear of the individual and ends 28, 30 of absorbent pledget 20 are similarly oriented directly below the crotch area. Ends 35, 48 are drawn towards the body surface by elastic members 58.

Absorbent core 16 desirably deforms about absorbent pledget 20 to form compartments 24 to facilitate flexibility such that absorbent article 10 forms a cup-like configuration about the body surface. During use, absorbent article 10 desirably deforms via compartments 24 conforming to the contour of the individual during wear, as discussed. Cooperation of absorbent pledget 20 and absorbent core 16 provide flexibility to absorbent article 10 to prevent undesired deformity thereof. Absorbent pledget 20 and absorbent core 16 absorb and retain fluid discharge. Other methods of use are also contemplated.

Figure 4:
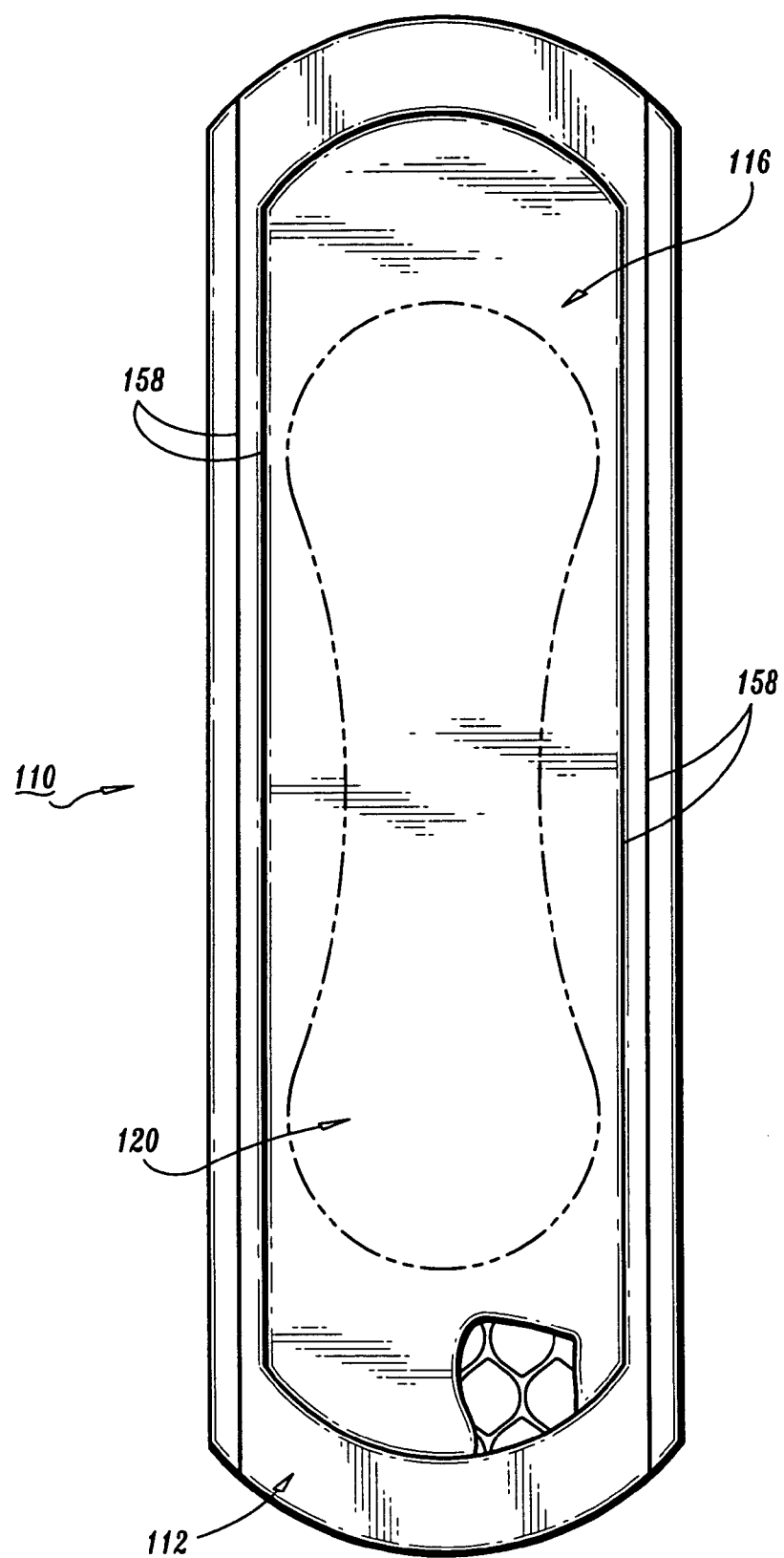
FIG. 4 is a top view of an alternate embodiment of the absorbent article shown in FIG. 1.

Referring to FIG. 4, an alternate embodiment of an absorbent article 110 is shown. Absorbent article 110, similar to absorbent article 10 discussed with regard to FIGS. 1–3, includes an elongated absorbent pledget 120 having a "dog-bone" or "hour-glass" like configuration. A coverstock 112 and an absorbent core 116 are also elongated to accommodate a larger body surface area. Elastic member 158 extends along the entire longitudinal length of coverstock 112. This configuration advantageously provides improved absorbency to applications for individuals with, for example, a larger thigh surface area.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. An absorbent article comprising:
   a fluid permeable coverstock configured to engage a body surface and defining longitudinal sides, the coverstock including a bi-component fiber having a polypropylene inner core and a polyethylene outer sheath;
   an absorbent core having a body facing side, an opposing side and extending longitudinally along the absorbent article, the absorbent core having arcuate outer ends and including wood pulp and superabsorbent polymer materials; and
   an absorbent pledget disposed between the absorbent core and the coverstock, the absorbent pledget including airlaid material adjacent to the body facing side of the absorbent core, the pledget further including a three dimensional apertured acquisition film mounted to the airlaid material and engaging the coverstock, the absorbent pledget having a greater structural stiffness and reduced surface area relative to the absorbent core, the absorbent core being configured to fold about the hourglass shape of the absorbent pledget and resist undesired deformity of the absorbent article; and
   where the coverstock includes adhesive coated elastic members disposed adjacent the longitudinal sides, the longitudinal sides being folded about a backsheet to enclose the absorbent core and absorbent pledget.

2. An absorbent article as recited in claim 1, wherein the absorbent pledget has a configuration contoured to engage a body surface.

3. An absorbent article as recited in claim 1, wherein the backsheet includes a polylaminate material.

4. An absorbent article comprising:
   an absorbent core;
   a topsheet and backsheet having respective edge portions in an overlapping relationship;
   at least one pair of elastic members adhesively bonded to longitudinal sides of the backsheet or topsheet; and
   an apertured film and airlaid substrate disposed between the absorbent core and the topsheet, wherein the airlaid substrate has a greater structural stiffness and a lower basis weight than the absorbent core.

5. The absorbent article of claim 4, wherein the absorbent core includes a superabsorbent material.

6. The absorbent article of claim 4, wherein the apertured film is substantially rectangular in shape.

7. The absorbent article of claim 4, wherein the airlaid substrate is dimensionally larger than the apertured film.

8. The absorbent article of claim 4, wherein the backsheet includes a laminate of a non-woven material and a polymeric film.

9. The absorbent article of claim 4, wherein the apertured film includes a three dimensional component in the direction of the backsheet.

* * * * *